United States Patent [19]

Humbert et al.

[11] 4,029,759

[45] June 14, 1977

[54] COMPOSITIONS CONTAINING COMPOUNDS PRODUCING A COOLING SENSATION

[75] Inventors: Francoise Ernestine Lucie Humbert, Paris; Yves Tollard D'Audiffret, Neuilly-sur-Seine, both of France

[73] Assignee: Lever Brothers Company, New York, N.Y.

[22] Filed: Feb. 15, 1973

[21] Appl. No.: 332,955

[30] Foreign Application Priority Data

Feb. 28, 1972 Luxembourg ......................... 64851

[52] U.S. Cl. ................................... 424/49; 424/16; 424/56; 424/73; 424/343; 132/89; 131/17 R; 131/202; 131/17 A; 252/32

[51] Int. Cl.² .......................................... A61K 7/16

[58] Field of Search ............................. 424/49–58; 260/631

[56] References Cited

FOREIGN PATENTS OR APPLICATIONS 123,909  9/1901  Germany
3,034    2/1915  United Kingdom ................. 424/52

Primary Examiner—Norman A. Drezin
Attorney, Agent, or Firm—Arnold Grant

[57] ABSTRACT

Compositions, particularly edible compositions, oral compositions and flavor compositions, containing a compound imparting a cooling sensation, said compound being a hydroxymethyl or hydroxyethyl derivative of para-menthane, for example 2-hydroxymethyl-menthol.

1 Claim, No Drawings

COMPOSITIONS CONTAINING COMPOUNDS PRODUCING A COOLING SENSATION

This invention relates to compositions containing compounds producing a cooling sensation. More particularly the invention concerns edible compositions, or compositions for topical application to a human being, or flavour compositions, which contain a compound producing a cooling sensation.

It is known that the appreciation of edible compositions and compositions for topical application to the skin can be enhanced by the inclusion therein of a compound producing a cooling sensation giving a sense of freshness or intensifying or prolonging the preception of freshness. Generally the fresh and cool physiological effect is achieved by the use of menthol which acts upon the nerve endings (terminals, receptors) responsible for temperature sensations. There is evidence that the cooling effect of menthol is caused by the fact that the nerves of the skin or mucous membrane which convey the perception of coldness are stimulated or show a stronger reaction to a decrease in temperature, such as in the oral cavity upon breathing, than would be the case in the absence of menthol. However, the use of menthol has certain disadvantages, for example the cooling sensation is not very long lasting.

It has now been found that the sensation of cooling and freshness can be imparted to various compositions by including in such compositions a para-menthane derivative of the general formula:

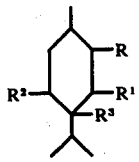

in which general formula
R = H when
  i. $R^1$ = OH, $R^2$ = H, and $R^3$ = —$(CH_2)_n$OH; or
  ii. $R^1$ = —$(CH_2)_n$OH, $R^2$ = H, and $R^3$ = OH; or
  iii. $r^1$ = OH, $R^2$ = —$(CH_2)_n$OH, and $R^3$ = H;
R = OH when $R^1$ = —$(CH_2)_n$OH, $R^2$ = H, and $R^3$ = H;
R = —$(CH_2)_n$OH when $R^1$ = OH, $R^2$ = H, and $R^3$ = H;
and $n$ = 1 or 2.

Preferred p-mentane derivatives for use in compositions according to the invention are 2-hydroxymethyl-mentol and 2-($\beta$-hydroxyethyl)-menthol, 3-hydroxymethyl-carvomenthol and 3-($\beta$-hydroxyethyl)-carvomenthol and the isomers of these compounds.

The above-identified p-menthane derivatives produce a cooling or freshness sensation similar to that produced by menthol, but without, however, certain of the disadvantages of menthol, such as burning. At suitable concentrations the compounds barely possess a distinctive flavour, but they cause a fresh sensation in the mouth which is retained for a considerable time. The p-menthane derivatives used in compositions according to the invention, produce a longer lasting sensation of freshness than does menthol.

Thus the use of the above p-menthane derivatives in compositions according to the present invention is an improvement over the use of menthol in that the duration of the cool and refreshing effect is prolonged and strengthed without any substantial flavour modification, aftertaste nor off-flavour being produced.

As is the case with methol, the above-defined p-menthane derivatives can be included in a wide variety of different products to impart thereto a sensation of cooling or freshness. In general terms, these comprise edible compositions, or compositions for topical application to a human being, or in flavour compositions, essential oils or perfumes for use in such compositions.

Examples of edible compositions with which the above p-menthane derivatives may be admixed are chocolate, bonbons, ice-creams, jellies, jams, margarine, alcoholic and nonalcoholic drinks, e.g. fruit juices and lemonade, and medicines. Compositions for topical application to the skin include aqueous and/or alcoholic lotions or creams, and cosmetic products such as lipsticks, as well as tobacco preparations for chewing, smoking or inhaling and filters for tobacco consisting of a fibrous or porous filter which may be impregnated with a p-menthane derivative of the above formula. A particular class of topically applied compositions to which the present invention relates are oral compositions, by which is meant a product in powder, paste or liquid form which on being used is retained for a time sufficient to contact the surface and the internal mucous membrane of the oral or nasal cavities or th pharynx. Such products include particularly those for the case of the oral cavity for example, mouth washes, dental and throat lozenges, gargles, chewing gum, dental creams or toothpastes, toothpicks, dental tablets and powders and topical solutions for application in dental treatment, as well as cough-mixtures, anti-acid and digestion promoting preparations and oral analgesics.

A further class of compositions with which the above p-menthane derivatives may be admixed are flavour compositions. In fact, it is often convenient to incorporate the defined p-menthane derivatives in, say, edible compositions and oral compositions, in admixture with a flavourant for such compositions. For instance, commonly used flavourants for dentifrices are peppermint and spearmint flavours. These will consist of a blend of different flavouring materials to which flavour compositions a p-menthane derivative may be added.

The most preferred compounds for use in compositions, in accordance with the invention are the 2-hydroxymethylmenthols, of which there are eight theoretically possible stereoisomeric forms.

The 2-hydroxymethylmenthols may be prepared in a manner known per se, such as described for example in German Patent Specification No. 123,909.

2-($\beta$-hydroxyethyl)-menthol may be prepared by alkylation of piperitone or of menthone enamine followed by chemical reduction of the keto-ester obtained.

3-($\beta$-hydroxyethyl)carvomenthol can be synthesised in the same way, starting from carvomenthone.

In the compositions according to the invention, it is generally convenient to use the compounds in the form of the mixture of the stereoisomers as they are obtained in the synthesis, unless explicity stated otherwise.

The duration and importance of the sensation of freshness may vary from one compound and consequently the optimum quantity to be used in each composition cannot be given exactly. Suitable effective amounts may, however, be determined by simple experimentation.

By way of illustration, we refer to the case where the p-menthane derivative is incorporated into a flavour composition. The amount of the flavour composition which may be included in, for instance, an edible composition or oral composition may, for example, be between about 0.5% and about 2% by weight typically resulting in from about 0.025% to about 1% by weight and preferably from about 0.1% to about 0.2% by weight of the p-menthane derivative in the total composition.

Dentrifrice compositions in accordance with the invention will comprise a base composition, comprising a substantially water-insoluble polishing material, a surface active agent, various additives and one or more of the above-defined p-menthane derivatives, preferably 2-hydroxymethylmenthol.

Suitable water-insoluble polishing materials or abrasives which may be employed are, for example, calcium carbonate, dicalcium phosphate, tricalcium phosphate, natural or synthetic silicas, alumina, hydrated alumina, calcium pyrophosphate, thermosetting resins, such as ureaformaldehyde or melamineformaldehyde resins, water-insoluble sodium metaphosphate, or suitable mixtures thereof. In general the content of polishing material is variable, but will generally be up to about 95% by weight of the total composition. In the case of a dental cream, the content of polishing material will generally be about 20 to 75%, preferably between 45 and 55%, whereas in tooth powders and dentals tablets, the content of polishing material will generally be higher, such as about 70 to 95% by weight.

Suitable surface active materials for use in dentifrice compositions are anionics, cationics, non-ionics, ampholytics or mixtures thereof. As anionic surface active materials that may be used in the oral compositions according to the invention may be mentioned: the soaps of higher fatty acids containing from 8 to 26 carbon atoms; the soaps of polycarboxylic acids as described in British Patent Specification No. 1,096,523; pure or mixed long-chain primary or secondary alkylsulphates, such as lauryl sulphate and the sulphates of higher fatty alcohols; the esters of sulphuric acid and polyhydric alcohols, partially esterified with higher fatty acids, for example the monosulplate of tallow monoglycerides; the sulphated alkanolamides of higher fatty acids; the alkyl ether sulphates,for example lauryl ether sulphate; the hydroxylsulphonates, esters of higher fatty acids; the esters of higher fatty acids and low molecular weight hydroxyalkane-sulphonic acids, for example the oleic acid ester of isethionic acid; the amides of higher fatty acids and amionalkane-ester of isethionic acid; the amides of higher fatty acids and aminoalkane-sulphonic acids, for example N-methyl-N-palmitoyl tauride; the water-soluble alkyl phosphates; the sulphated condensation products of alkylene oxides with hydrophobic materials as described below; the sulphosuccinic esters, such as dioctylsuccinate; the sulphonated higher fatty acids; the sulphonated oils; the olefin sulphonates; the sulphonates of alkylaromatic hydrocarbon compounds possesing an alkyl substituent containing from 8 to 26 carbon atoms (with a mono- or polynuclear structure). Examples of suitable cationic surface active materials are alkylamine salts; quaternary ammonium salts; acylalkanolamine salts, the aliphatic acyl amides of saturated aliphatic monoaminocarboxylic acids having 2 to 6 carbon atoms and in which the acyl radical contains from 12 to 18 carbon atoms, such as sodium N-lauroyl sarcoside. As nonionic surface active materials that can be used in the oral compositions according to the invention may be cited: the condensation products of alkylene oxides with hydrophobic compounds such as higher fatty alcohols, polyhydric alcohols, alkylphenols; products of the reaction of propylene oxide with ethylene diamine, fatty acid amines, amides of alkanesulphonic acids, substituted polyamines, polypropylene glycols, etc. Other nonionic products are the products of the condensation of fatty acid chlorides with hydrolysed natural proteins; esters of higher fatty acids and sugars, e.g. sucrose palmitate. The ampholytic surface active materials that can be used are the salts of N-alkylated compounds of β-aminopropionic acid, imidazolines, betaines, sultaines, etc.

The surface active materials are preferably used in the form of their water-soluble salts such as salts or alkali metals (for example sodium, potassium), or of ammonium, and also in the form of salts of nitrogen-contaiing bases like the low molecular weight alkanolamines sch as mono-, di- and triethanolamines. It is also possible to use mixtures of different salts . The content of surface active material is in general from 0.01 to 10% by weight of preferably from 0.5 to 5% by weight of the total oral composition.

In dental cream preparations the liquid and solid constituents of the compositions should be in proportions such that a creamy mass of the desired consistency is formed which is extrudable from an aerosol container or a collapsible tube. In this case a humectant is used, for example glycerol or sorbitol, and a binder or thickener, such as gum tragacanth, gum karaya, gum arabic, sodium carboxymethylcellulose, hydroxyethylcellulose, polyvinyl pyrrolidone, starch, Irish moss, alginates, bentonite and collodial magnesium aluminum silicate. The amount of thickener is generally up to 10% and preferably 0.2 to 55 by weight of the total composition.

Furthermore, whiteners, such as titanium dioxide; optical brighteners; bleaching agents; various ammoniated ingredients, such as urea, diammonium phosphates; astringents; chloroform; additional humectants e.g. propylene glycol or other polyhydric alcohols; film-forming substances, such as silicones; enzymes; harmless colouring materials; germicides, such as dichloro- or hexachlorophene; vitamins, such as those of the B-group; preservatives, such as sodium benzoate; anti-biotic agents; corrosion inhibitors; chlorophyl derivatives; cariostatic agents such as stannous fluoride, sodium monofluorophosphate, alkali metal fluorides; may also be incorporated in oral compositions according to the present invention. The amount of cariostatic or antimicrobial agents in dental pastes is generally from 0.01 to 1% and preferably from 0.02 to 0.5% by weight of the total composition. Generally the amount of flavouring material is from 0.01 to 5% or more by weight of the total composition.

In addition to the flavouring composition, small amounts of sweetening agents, such as saccharin, dextrose, levulose and sodium cyclamate, may also be incorporated in the compositions according to the present invention. The amount is generally from 0.01 to 5% by weight of the total composition.

The pH of the compositions according to the present invention must be within a range practicable for use. This range is from about 4 to 8, preferably of about 4.5 to 6.5. Acidifying agents, such as citric acid, which are suitable for use in the oral cavity, can be added to the composition to adjust and maintain the pH within the desired range.

As remarked earlier, the 2-hydroxymethylmenthols (or other p-menthane derivative) are conveniently included, in the case of dentifrices and certain other compositions, along with the flavour composition. They may however be added separately and at any stage of the manufacture of the dentifrice, either in solution or in solid form. They may be used in encapsulated form or adsorbed on a carrier.

The following examples are of compositions in accordance with the invention. Examples 1 to 4 are of flavour compositions.

EXAMPLE 1

| Aniseed flavour | % by weight |
|---|---|
| Natural anethole | 23 |
| Synthetic anethole | 22 |
| Ceylon cinnamon oil | 3 |
| Bulgarian mint oil | 27 |
| Natural menthol crystal | 10 |
| 2-hydroxymethylmenthol | 15 |

EXAMPLE 2

| Spearmint flavour | % by weight |
|---|---|
| Spearmint USA oil | 64.0 |
| Bulgarian mint oil | 8.0 |
| Natural menthol | 6.0 |
| Resinous benzoin | 0.1 |
| Cloves oil | 1.3 |
| Ceylon cinnamon oil | 0.1 |
| Anethole from Chinese aniseed | 3.3 |
| 2-hydroxymethylmenthol | 17.0 |
| Sweet fennel oil | 0.2 |

EXAMPLE 3

Instead of a mixture of the isomers of 2-hydroxymethylmenthol, the trans-2-hydroxymethylmenthol is included in the composition of Example 2.

EXAMPLE 4

| Peppermint flavour | % by weight |
|---|---|
| Bulgarian mint oil | 32.0 |
| Arvensis mint oil | 34.0 |
| Menthol | 5.0 |
| Natural anethole | 4.0 |
| Wintergreen | 1.0 |
| Thymol | 2.0 |
| Essence of cloves | 0.2 |
| Vanilla tincture | 1.7 |
| Ceylon cinnamon oil | 0.1 |
| 2-hydroxymethylmenthol | 20.0 |

EXAMPLE 5

| Toothpaste with peppermint flavour | % by weight |
|---|---|
| Calcium carbonate | 45.7 |
| Starch | 7.0 |
| Glycerol | 28.2 |
| Water | 14.6 |
| Sodium benzoate | 2.2 |
| Flavour of Example 4 | 1.0 |
| Sodium saccharinate | 0.3 |
| Sodium lauryl sulphate | 1.0 |

EXAMPLE 6

| Toothpaste with spearmint flavour | % by weight |
|---|---|
| Dicalcium phosphate dihydrate | 40.0 |
| Tricalcium phosphate | 6.0 |
| Sodium lauryl sulphate | 1.8 |
| Glycerol | 20.0 |
| Sorbitol syrup (70%) | 8.0 |
| Sodium carraghenate | 1.2 |
| Saccharine solution (10%) | 1.4 |
| Ethylhydroxybenzoate | 0.1 |
| Flavour of Example 3 | 1.5 |
| Water | 20.0 |

EXAMPLE 7

| Toothpaste with spearmint flavour | % by weight |
|---|---|
| Aluminium hydroxide Al(OH)$_3$ (microcrystalline) | 42.50 |
| Alumina (Al$_2$O$_3$) | 2.00 |
| Glycerol | 28.00 |
| Water | 24.50 |
| Sodium lauryl sulphoacetate | 1.00 |
| Flavour of Example 2 | 1.00 |
| Tragacanth | 0.50 |
| Methyl-p-hydroxybenzoate | 0.10 |
| Saccharin, soluble | 0.05 |
| Phosphoric acid (H$_3$PO$_4$ 100%) sufficient to produce a pH value of 6.5–7.5 | |

EXAMPLE 8

| Toothpaste with aniseed flavour | % by weight |
|---|---|
| Calcium pyrophosphate | 42.2 |
| Sodium lauryl sulphate | 1.3 |
| Glycerol | 25.0 |
| Water | 29.0 |
| Gum tragacanth | 1.4 |
| Sodium fluoride | 0.2 |
| Flavour of Example 1 | 0.9 |

EXAMPLE 9

| Toothpaste with spearmint flavour | % by weight |
|---|---|
| Insoluble sodium metaphosphate | 26.6 |
| Dicalcium phosphate | 26.6 |
| Gum | 1.4 |
| Flavour of Example 3 | 1.6 |
| Sodium lauryl sulphate | 1.1 |
| Glycerol and water | 42.7 |

EXAMPLE 10

| Toothpaste with peppermint flavour | % by weight |
|---|---|
| Silica | 22.0 |
| Glycerol | 58.0 |
| Water | 17.5 |
| Sodium alkyl sulphate | 1.5 |
| Flavour of Example 4 | 1.0 |

EXAMPLE 11

| Tooth powder | % by weight |
|---|---|
| Insoluble sodium metaphosphate | 76.8 |
| Tricalcium phosphate | 20.0 |

-continued

| Tooth powder | % by weight |
| --- | --- |
| Sodium lauryl sulphate | 1.0 |
| Flavour of Example 2 | 2.0 |
| Saccharine | 0.2 |

EXAMPLE 12

| Solid dentifrice | % by weight |
| --- | --- |
| Dental soap | 18 |
| Abrasive materials (usually chalk) | 79 |
| Glycerine | 3 |
| Colour | q.s. |
| Flavour of Example 1 | q.s. |
| Sweetener | q.s. |

EXAMPLE 13

| Mouthwash concentrate | % by weight |
| --- | --- |
| Sodium saccharinate | 2.000 |
| Propylene glycol | 25.000 |
| Glycerol | 25.000 |
| Polyoxyethylene sorbitan monooleate | 20.000 |
| Colour | 0.075 |
| Ethyl alcohol | 26.175 |
| Flavour of Example 4 | 1.750 |

EXAMPLE 14

| Toothpaste with aniseed flavour | |
| --- | --- |
| Composition: Ingredients | % by weight |
| Water | 28.1 |
| Glycerine | 15.0 |
| Sodium saccharinate | 0.1 |
| Dicalcium phosphate | 26.6 |
| Sodium carraghenate | 1.4 |
| Insoluble sodium metaphosphate | 26.6 |
| Sodium lauryl sulphate | 1.2 |
| Aniseed flavour composition | 1.0 |
| Aniseed flavour composition | % by weight |
| Natural anethole | 26 |
| Synthetic anethole | 26 |
| Ceylon cinnamon oil | 3 |
| Bulgarian mint oil | 39 |
| Resinous benzoin | 1 |
| Natural menthol | 5 |

To measured quantities of this toothpaste, 0.15%, 0.20% and 0.25% of 2-hydroxymethylmenthol were added in the usual manner to give pastes A, B and C, respectively, and the freshness of these pastes was compared with the control paste, i.e. the paste to which no addition had been made. The fresh sensation of toothpaste A, B and C on brushing the teeth was stronger than that of the control paste and remained longer. The duration of the freshness of the control paste was 15 minutes, that of the test samples of A, B and C was 21, 25 and 28 minutes, respectively. The control paste and the three test pastes were then stored for 3 weeks at room temperature, after which the freshness was again tested and compared with the control paste. The freshness of the control paste remained 15 minutes, while the pastes A, B and C also kept their fresh sensation for, respectively, 21, 25 and 28 minutes.

EXAMPLE 15

| Toothpaste with spearmint flavour | |
| --- | --- |
| Composition: Ingredients | % by weight |
| Water | 16.9 |
| Glycerine | 30.6 |
| Sodium saccharinate | 0.2 |
| Calcium carbonate | 12.1 |
| Sodium carraghenate | 1.5 |
| Dicalcium phosphate | 36.2 |
| Sodium lauryl sulphate | 1.5 |
| Spearmint composition | 1.0 |
| Spearmint flavour composition | % by weight |
| Spearmint USA | 48.0 |
| Bulgarian mint oil | 30.0 |
| Natural menthol | 0.2 |
| Resinous benzoin | 0.1 |
| Essence of cloves | 0.4 |
| Ceylon cinnamon oil | 0.1 |
| Anethole from Chinese aniseed | 0.4 |
| Clary | 0.2 |
| Sweet fennel | 0.3 |
| Powdered lemon bark | 0.5 |

To measured quantities of this toothpaste, 0.15%, 0.20% and 0.25% of 2-hydroxymethylmenthol were added in the usual manner and the fresh sensation of these pastes, indicated as A, B and C, was compared with the above control paste. The freshness of A, B and C was stronger than that of the control and remained longer. The duration of the freshness of the control paste was 15 minutes, that of the test samples of A, B and C was 20, 23 and 25 minutes, respectively. The control paste and the three test pastes were then stored for 3 weeks at room temperature, after which the freshness was again tested and compared with the control. No loss was noted. The freshness of the control remained for 15 minutes, while the pastes A, B and C also kept their fresh sensation for, respectively, 20, 23 and 25 minutes.

EXAMPLE 16

| Lipstick | % by weight |
| --- | --- |
| Beeswax | 5.0 |
| Candelilla wax | 22.0 |
| Oleic alcohol | 39.0 |
| Vaseline oil | 24.5 |
| Pigments | 8.0 |
| Perfume | 0.5 |
| 2-hydroxymethylmenthol | 1.0 |

This lipstick gives a distinct fresh sensation on the lips.

EXAMPLE 17

Chocolate bonbons 259 g chocolate is melted in a casserole and two spoonfuls of milk are added. 100 g butter is further added. The heating is stopped and subsequently two egg-yolks and 0.035 g 2-hydroxyethylmenthol are introduced. The paste is allowed to stand until the consistency is such that truffles can be made.

The sensation of freshness without the smell of menthol blends very well with the flavour of chocolate.

EXAMPLE 18

| Eye wash | % by weight |
| --- | --- |
| Witch hazel | 25.000 |

| Eye wash | % by weight |
| --- | --- |
| Boric acid | 2.000 |
| Sodium borate | 0.500 |
| Salicylic acid | 0.020 |
| Phenyl mercury borate | 0.002 |
| Water to | 100.000 |

0.02% 2-hydroxymethylmenthol, calculated on the total weight, is added to the composition. When it is used as eyebath, a sensation of freshness is observed on the eye-ball and the eye-lids.

EXAMPLE 19

| Gargle | % by weight |
| --- | --- |
| Sodium salicylate | 1.6 |
| Resorcin | 1.6 |
| Chloral | 5.0 |
| Glycerol | 10.0 |
| Flavour | 0.5 |
| Water to | 100.0 |

1.5% 3-hydroxymethylcarvomenthol is added to the concentrated solution. When it is diluted with approximately 10 times its volume of water and is used for mouth rinsing, a prolonged sensation of freshness is observed.

EXAMPLE 20

| Concentrated soft drink | % by weight |
| --- | --- |
| Lemon juice | 35.000 |
| Saccharose | 11.000 |
| Colourant | 0.025 |
| Citric acid | 0.280 |
| Sodium benzoate | 0.015 |
| Water to | 100.000 |

0.25% 2-hydroxymethylmenthol is added to the concentrate. The concentrate is diluted with water and tasted. This drink gives a fresh effect. The lemon flavour is not denatured by the addition of 2-hydroxymethylmenthol.

EXAMPLE 21

Tobacco for cigarettes

Tobacco for cigarettes of a commercially available brand is pulverised with a solution of 3-hydroxymethylcarvomenthol in ethanol and is used for rolling cigarettes containing each about 50 mg of the active compound. When the impregnated cigarettes are smoked, the sensation of freshness is observed in the mouth which is characteristic of mentholated cigarettes, but no odour other than that normally associated with tobacco is observed.

EXAMPLE 22

Filter ends of cigarettes

The filter end of cigarettes of a commercially available brand is impregnated in a solution of 2-hydroxymethylmenthol in a quantity sufficient to deposit 0.02 mg of the active compound in the filter. When cigarettes with the impregnated end are smoked, a distinct sensation of freshness is observed in the mouth.

EXAMPLE 23

| Strawberry jam | % by weight |
| --- | --- |
| Saccharose | 62.0 |
| Strawberries | 33.4 |
| Solution of peptin (5%) | 4.0 |
| Solution of tartaric acid (50%) | 0.6 |
| Water to | 100.0 |

These ingredients were thoroughly mixed and the whole was cooked until a jam of good consistency was obtained. The jam was allowed to cool down and was thoroughly mixed with 0.03% 2-hydroxymethylmenthol. The effect was that the jam gave a distinctly fresher and less sweet taste than jam to which no hydroxymethylmenthol was added. This was observed by 10 members of a panel consisting of 12 persons who tested the jam spread on slices of bread and butter.

EXAMPLE 24

Margarine

To a commercially available margarine mixture 0.01% 2-hydroxymethylmenthol was added and thoroughly mixed therewith. The taste of the mixture was subsequently compared with that of the commercially available margarine to which nothing had been added. The margarine mixture with 2-hydroxymethylmenthol was found to have a cooler effect in the mouth than the same margarine to which no addition had been made.

EXAMPLE 25

| Orange drink | % by weight |
| --- | --- |
| Saccharose | 11.000 |
| Citric acid | 0.280 |
| Sodium benzoate | 0.015 |
| Colourant | 0.025 |
| Orange flavour | 0.050 |
| 2-hydroxymethylmenthol | 0.020 |
| Water to | 100.000 |

This drink gives a fresh effect and the taste is not denatured by the addition of 2-hydroxymethylmenthol.

EXAMPLE 26

| Aerated lemonade (carbonated soft drink) | % by weight |
| --- | --- |
| Saccharose | 11.00 |
| Citric acid | 0.13 |
| Water to | 100.00 |

At a temperature of 10° C, carbon dioxide is introduced into the mixture of the above ingredients having a pH of 2.7 until the pressure of the carbon dioxide is 2.24 kg/cm$^2$. Some more flavours and colourants and subsequently added to the mixture and 0.03% hydroxymethylmenthol is dissolved therein. When drinking this aerated lemonade, one gets the impression that the drink is cooler than it really is.

EXAMPLE 27

| Dessert product | % by weight |
| --- | --- |
| Skim milk powder | 30.00 |
| Sucrose | 30.00 |
| Precooked starch | 3.00 |

-continued

| Dessert product | % by weight |
| --- | --- |
| Glucono-γ-lactone | 12.25 |
| Citric acid monohydrate | 1.00 |
| Flavouring and colouring | 0.20 |
| Milk | 284 ml |

To this mixture 0.02% hydroxymethylmenthol was added. The product had a distinct cooling effect on the palate.

The above-mentioned Examples illustrate the range of compounds and compositions falling within the scope of the invention without being limited thereto.

What is claimed is:

1. A method for imparting a cooling property to a composition for the care of the oral cavity comprising the step of adding to the composition from about 0.025 to about 2 percent by weight of the composition of a compound selected from the group consisting of 2-hydroxymethylmenthol, 2-(β-hydroxy ethyl)-menthol, 3-hydroxymethylcarvomenthol and 3-(β-hydroxy ethyl)-carvomenthol.

* * * * *